United States Patent
Kerr et al.

(10) Patent No.: US 11,730,431 B2
(45) Date of Patent: *Aug. 22, 2023

(54) INJECTABLE VASCULAR ACCESS PORT WITH DISCERNABLE MARKERS FOR IDENTIFICATION

(71) Applicant: PFM Medical, Inc., Carlsbad, CA (US)

(72) Inventors: Marshall Kerr, Carlsbad, CA (US); Alain Rosier, Carlsbad, CA (US); Donn K. Harms, Del Mar, CA (US)

(*) Notice: Subject to any disclaimer, the term of this patent is extended or adjusted under 35 U.S.C. 154(b) by 606 days.

This patent is subject to a terminal disclaimer.

(21) Appl. No.: 16/730,638

(22) Filed: Dec. 30, 2019

(65) Prior Publication Data
US 2020/0155085 A1     May 21, 2020

Related U.S. Application Data

(60) Division of application No. 13/423,068, filed on Mar. 16, 2012, now abandoned, which is a continuation-in-part of application No. 12/700,695, filed on Feb. 4, 2010, now Pat. No. 10,022,094.

(60) Provisional application No. 61/149,967, filed on Feb. 4, 2009.

(51) Int. Cl.
*A61B 6/12*     (2006.01)
*A61M 39/02*     (2006.01)

(52) U.S. Cl.
CPC ............ *A61B 6/12* (2013.01); *A61M 39/0208* (2013.01); *A61M 2039/0238* (2013.01); *A61M 2205/6036* (2013.01); *A61M 2205/6054* (2013.01); *G06V 2201/034* (2022.01)

(58) Field of Classification Search
CPC ................ A61B 6/12; A61M 39/0208; A61M 2039/0238
See application file for complete search history.

(56) References Cited

U.S. PATENT DOCUMENTS

| | | | | |
|---|---|---|---|---|
| 6,287,293 B1* | 9/2001 | Jones | ................ | A61M 39/0208 604/502 |
| 2006/0264898 A1* | 11/2006 | Beasley | ................... | A61B 6/12 428/36.9 |
| 2007/0282196 A1* | 12/2007 | Birk | ...................... | A61F 5/0003 600/424 |

* cited by examiner

*Primary Examiner* — Bradley J Osinski
(74) *Attorney, Agent, or Firm* — Donn K. Harms

(57) ABSTRACT

An improved injection port identification for injection ports implanted under the skin of a patient. The injection port has an x-ray discernable marker allowing for the determination of a pressure rating for the injection port when so implanted. A plurality of concurrent visual, RF, light emitting and sonic means for signaling the port's pressure rating are also employable to provide multiple concurrent affirmations of the port's readiness for high pressure injections.

12 Claims, 3 Drawing Sheets

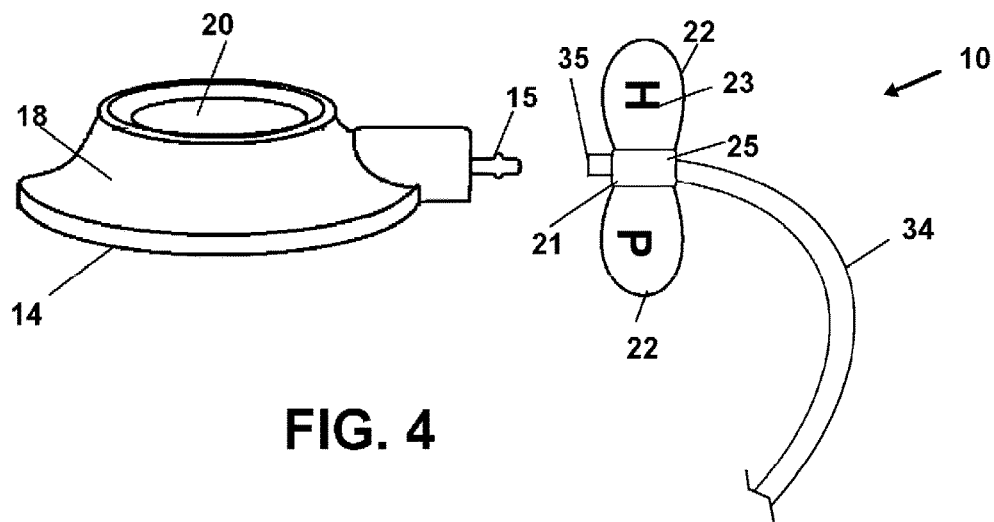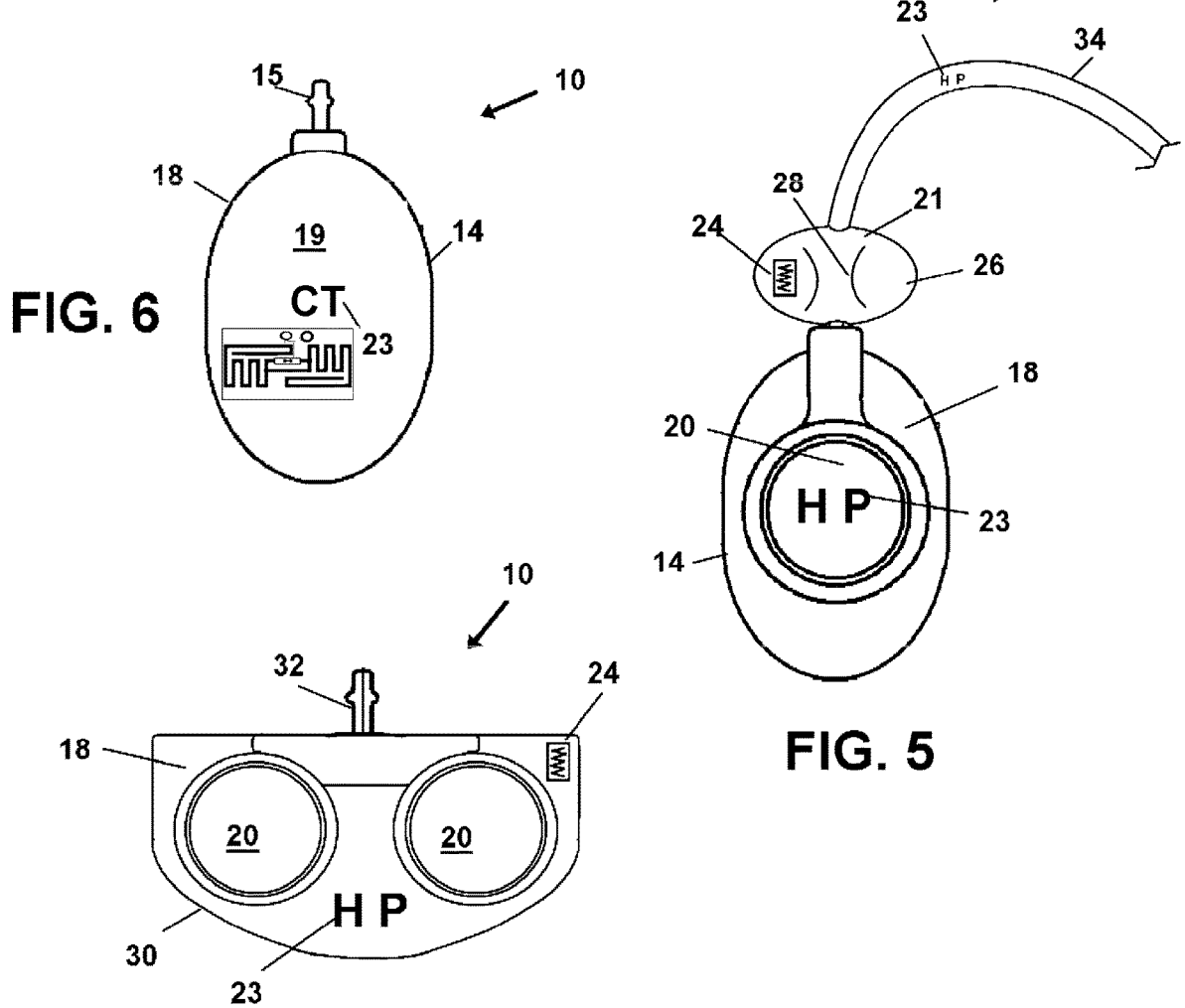

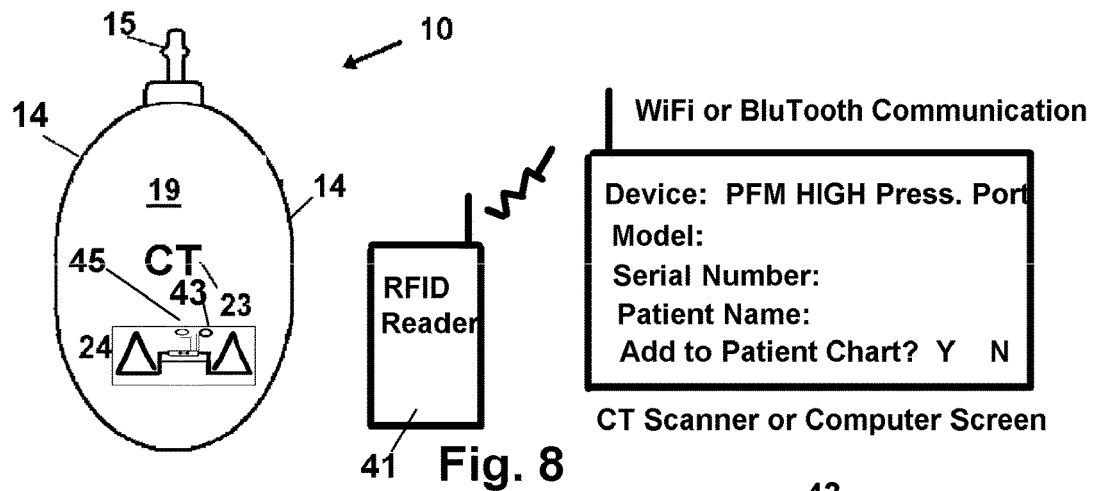
Fig. 8
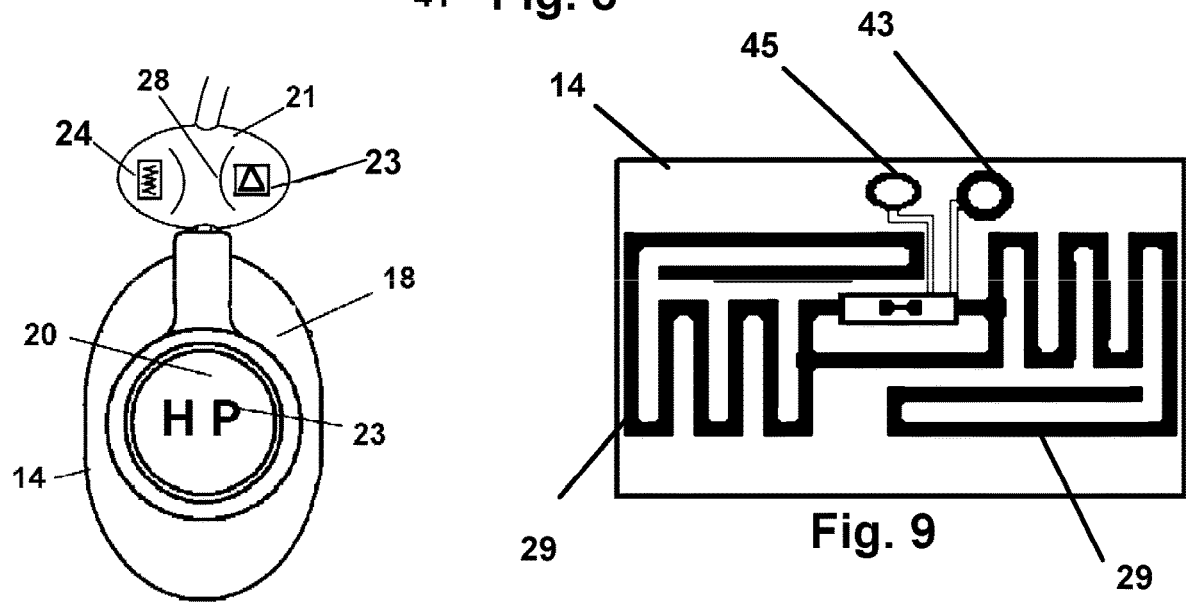
Fig. 9
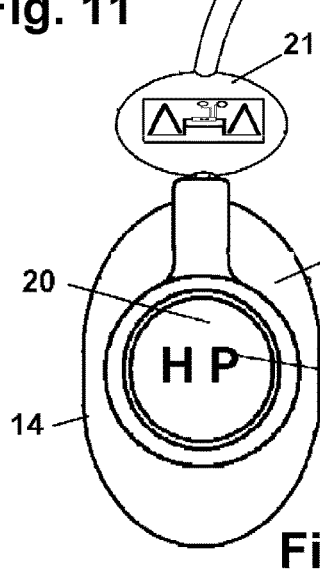
Fig. 11
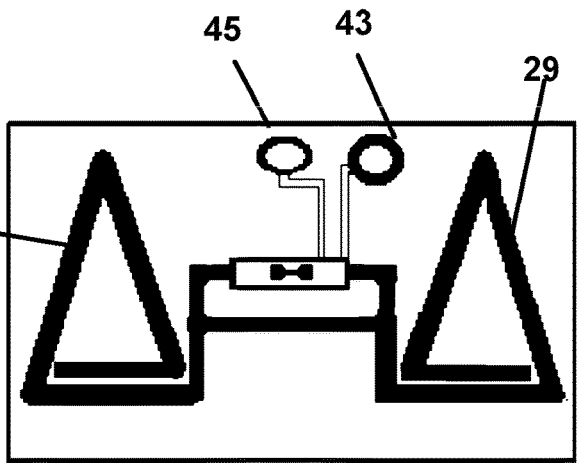
Fig. 10
Fig. 12

INJECTABLE VASCULAR ACCESS PORT WITH DISCERNABLE MARKERS FOR IDENTIFICATION

FIELD OF THE INVENTION

This application is a divisional application of U.S. application Ser. No. 13/423,068 filed on Mar. 16, 2012, which is a Continuation in Part of U.S. application Ser. No. 12/700,695 filed on Feb. 4, 2010 which claims the benefit of U.S. Provisional Application Ser. No. 61/149,967 filed on 4 Feb. 2009, both herewith included in their respective entirety by this reference thereto.

The disclosed device relates to power-injectable vascular access ports which are implanted in a patient and conventionally employed for powered injection of medicine and medical related injectables such as during an injection of contrast media for a CT scan. More particularly, it relates to such a vascular access port which provides users one or a plurality of pressure rating markers which may be X-ray discernable, audible, discernible using RF energy for digital reporting, or through visual observation of the skin. Pressure rating is determinable using one or a plurality of the discernible markers to ascertain the port itself is rated for powered injection under high pressure.

BACKGROUND OF THE INVENTION

Intravenous therapy or IV therapy is the giving of liquid substances directly into a blood vessel. Such therapy may be intermittent or may be continuous and during the therapy a fluid conduit must be established into the vascular system of the patient and maintained.

The simplest form of intravenous access is a syringe with an attached hypodermic needle. The needle is inserted through the skin into a blood vessel, and the contents of the syringe are injected through the needle into the bloodstream. Since direct injection only allows for the delivery to a patient of a single dose of medication, where prolonged therapy using multiple doses is to the regimen, a more popular mode employs a peripheral IV line consisting of a short catheter (a few centimeters long) inserted through the patient's skin into a sealed engagement with a peripheral vein. A body or hub in sealed communication with the axial passage of the catheter is engaged on the distal end of the catheter and remains outside the patient's body, usually on the skin surface. In this position the hub can be connected to a syringe or an intravenous infusion line to communicate fluid to the bloodstream of a patient, or capped when not in use. The hub and engaged catheter thus allows for multiple treatments with the same line.

However, on many patients a more direct route to the central blood vessels is required for provision of medication, treatments, and injections employed during X-ray and other imaging. Conventionally, a central venous line provides access for this purpose and consists of a catheter being inserted into a subclavian, internal jugular, or (less commonly) a femoral vein and advanced toward the heart until it reaches the superior vena cava or right atrium. Because all of these veins are larger than peripheral veins, central lines can be employed to deliver a much higher volume of fluid and can also have multiple lumens feeding the central line.

Implantable ports are a type of central venous line which does not employ an external connector positioned outside the patient's body. Instead, such implantable ports have a small reservoir which is covered with a flexible cover and the entire device is implanted under the skin of the patient. A catheter or other means for sealed communication of a lumen between a blood vessel and the reservoir, communicates between an outlet of the reservoir and an internal blood vessel such as a vein. Often, a rigid cap or similar capping means is employed with the communication means to further secure the distal end of the catheter to the reservoir outlet. Such a cap known in the art is typically a small cylindrical member that is slidably and coaxially engaged upon the lumen or catheter enhancing the coaxially fictional engagement of the catheter to the outlet. In use, the rigid cap is slidably engaged upon the catheter surface by sliding it over the catheter which is engaged around the outlet. A force imparted circumferentially to the catheter by the cap, sandwiches the catheter between the cap and the conduit over which it engages and thereby acts to further bias the catheter against its contact with the outlet, and securely engage the catheter to the outlet exterior surface.

Once so implanted, medication may be administered to the patient thereafter by communicating a small huber needle through their skin, piercing the septum or flexible cover of the port, and injecting the medication directly into the reservoir under the flexible cover provided by the septum. When the needle is withdrawn, the reservoir cover, which is formed of a material which reseals, seals itself.

Since the septum formed by the implanted port reservoir cover can accept hundreds of needle piercings during its lifetime, it is possible to leave the port in the patient's body for years. This semi-permanent implantation under the skin, helps avoid infection by leaving the skin barrier intact. Further, over time employment of the implant is much less painful to the patient since they need not endure pokes and needle sticks and the incision generally required by exterior mounted ports.

However, a particular problem occurs for medical professionals during the implantation process with many conventional ports. During assembly, the secure engagement of the reservoir outlet to the catheter can be particularly troublesome. This difficulty is caused by the relatively small size of the cap which must be held by the gloved hand of the medical professional. It is often difficult to grip the small cap and slide it along the catheter and over a sealing bulge in the outlet conduit to correctly and securely engage the cap circumferentially around and to the catheter which itself is engaged to the tubular conduit providing the outlet. The friction of the catheter against the inside circumference of the cap can cause the cap to slip from the user's fingers.

The problem is further exacerbated because the professional is wearing gloves, and the cap and catheter can become wet and slippery. This combination of circumstances often causes the medical professional to drop the cap which becomes non-sterile on landing, wherein it must be immediately discarded. This problem is sufficiently prevalent that some manufacturers provide a plurality of caps with the kit of the implantable port.

If the medical professional is able to correctly engage the cap over and onto the catheter and secure it to the tube forming the outlet, there is an additional problem which occurs when implantable ports are to be infused using power injection. Such infusions communicate the liquid into the reservoir of the implanted port, under high pressure, in order to move a large amount of liquid into the body of the patient in a short time. Such powered injection devices communicate fluid at high pressure levels through the septum covering the reservoir of the implanted infusion port which must be rated to handle the high pressure or the port could malfunction. The user must ascertain before such a high pressure injection, that the implanted port is rated for the anticipated high fluid pressure or a rupture of the port and related serious problems will occur.

Because the implanted port is positioned under the skin of the patient, conventionally there is no means for the professional to visually inspect it and ascertain a pressure rating during and after use. Consequently, it can be a vexing task for medical personnel to ascertain if in fact an implanted port is rated for high pressure and the communication of a high volume of the anticipated infusion to be given the patient. Hidden from view by the patient skin layer, it is conventionally not possible to examine the implanted port prior to use and ascertain visually the port is rated for the upcoming procedure.

However, because of the potential for patient harm should a rupture occur, most medical protocols require two independent means of ascertaining the implanted port is high-pressure rated. The dual confirmation must be ascertained prior to using the port during a subsequent high pressure injection through the septum covering the reservoir of the port. Currently, one means to ascertain the port pressure rating is to read the patient's chart which may be marked with the pressure rating on the hidden port. Another means is to look for and read exterior identification means where the patient may wear an ID bracelet, or other means to denote that the implanted port is rated to the pressure to which it is about to be connected.

However, there is currently no means for visual confirmation of the implanted and skin-covered port's pressure rating by an inspection of the implant site by the medical professional. Consequently, they must depend upon the accurate charting and labeling by themselves and by other workers. With charts and bracelets being known to be less than accurate on occasions, or in cases where a chart indicates one pressure rating and a bracelet indicates another, it would be especially helpful to provide one or a combination of alterative means to ascertain the pressure rating of an implanted port. In cases where the records and charts disagree, multiple alternative pressure determination means would also prevent needless patient procedures to remove or replace implanted ports when two means of identification cannot be found. Further, all of this confirmation required slows the progress of CT scans for the patient which costs the medical facility valuable time where the scanner by be employed elsewhere.

As such, there exists a continual unmet need, for a means for medical professional to identify that an implanted infusion port, hidden by skin and other patient tissue, is actually rated for the high pressure use for which it is about to be employed. Such a means of identification should be easy to employ, and allow for the use of the installed base of medical equipment already in hospitals and medical offices to lower costs and insure widespread easy deployment. Such means for identification should ideally provide a plurality of means to ascertain a high pressure rating on the implanted port to allow the medical professional to choose a favorite or supplement another determinable means on the port.

In addition to the need to better identify the ports pressure ratings, there is a further unmet to need for an improved means for engaging the cap member to the catheter to insure its secure engagement to the outlet conduit of the port. Such an improved securing means should employ a similar procedure as the current cap engagement to the catheter to thereby encourage use by not requiring the learning of a new skill. Further, such an improved engagement should eliminate the dropping of conventional clips and the need to provide multiple clips for that eventuality and to provide an improved gripping means for the cap that will more easily allow the user to grasp it even while wearing gloves.

With respect to the above, before explaining at least one preferred embodiment of the invention in detail or in general, it is to be understood that the invention is not limited in its application to the details of construction and to the arrangement of the components or the steps set forth in the following description or illustrated in the drawings. The various apparatus and methods of the invention are capable of other embodiments, and of being practiced and carried out in various ways, all of which will be obvious to those skilled in the art once the information herein is reviewed. Also, it is to be understood that the phraseology and terminology employed herein are for the purpose of description and should not be regarded as limiting.

As a consequence, those skilled in the art will appreciate that the conception upon which this disclosure is based may readily be utilized as a basis for designing new X-ray or fluoroscope discernable markers, and combinations of other visual, sonic, and RF enabled markers, allowing for a power and a pressure rating verification of implanted infusion ports and the like, and for carrying out the several purposes of the present disclosed device and method. It is important, therefore, that the embodiments, objects and claims herein, be regarded as including such equivalent construction and methodology insofar as they do not depart from the spirit and scope of the present invention.

SUMMARY OF THE INVENTION

The marker device allowing the identification method herein is employed in combination with an injection port (or portacath) which is a small medical appliance that is conventionally installed beneath the skin. Such ports are designed for implantation under the skin of a patient and the port employs a septum or membrane cover on an upper surface closest to the patient's skin. This septum or cover provides a self-sealing means to communicate with an underlying reservoir and is adapted to be pierced by a needle or other means to communicate medicine and drugs into the underlying reservoir or for the taking of blood samples therefrom on numerous occasions.

The marker device allowing for identification of the implanted port, is engaged to, or within, the implanted port and is formed of a material such as nitinol or tungsten or titanium, or stainless steel, or other non-ferrous metal which can easily be discerned on a CT scan or X-ray or on a fluoroscope. In a preferred mode, the marker is placed within the reservoir of the port. Such as location is preferable in that there is know chance of the marker be scraped off or otherwise damaged during instillation or removal within a patient.

In other preferred modes however, the marker device may be any X-ray discernable material such as a high density ceramic, or X-ray excitable polymer. The marker may be a planar piece of material that is positioned within the interior of the reservoir, or upon the exterior of the septum cover or implanted port, or it may be a piece of the preferred discernable material which is free floating within the reservoir cavity within the implanted port. Other materials which will be substantially discernable on an x-ray, may be employed such as ink infused with metallic material such as a high density ceramic, an x-ray excitable polymer, titanium, stainless steel, or other non-ferrous metal and which may be imparted to an interior or exterior surface of the implanted port. Still further, the marker device formed employing such an ink may also be imparted on the conduit, septum, or for ease of reading without the port body obscuring it, the marker may be positioned on the conduit cap of the implanted port.

It is most preferred that a visual marker employ a non-alphanumeric identifier because some technicians may have trouble reading letter and numbers indicating pressure ratings. Further, such ports are employed in many countries with many languages, and the use of letters and words in one country may not be understandable in another. Still further, in some countries, x-ray technicians may not be able to read at all and the use of letters or number designators will not provide information to such users that a simple symbol can.

It is preferred therefor that the symbol be singular in nature so as not to be confusing and a simple shape that is easily discerned. A current preferred symbol is that of a triangle as rectangles and multiple sided figures are easily confused when reading them. A triangle on the other hand is the only three sided shape, is readily identifiable by technicians who read, and those that are illiterate.

In use, the metal triangle is placed free floating in the reservoir as a simple universal marker to identify an implanted port as high pressure rated. During a CT scan, which concurrently requires the injection of a large volume of liquid by a power injection under high pressure, the medical professional performing the procedure, even if illiterate, can easily first ascertain if the implanted port has the high pressure rating required for the procedure. The user can do so quickly by simply taking a quick X-ray of the patient in the vicinity of the implanted port. If the port is pressure rated for the procedure, the triangle shaped formed of the material which will show on the X-ray, will be easily discernable on the X-ray as engaged to or within the plastic implanted port. This will provide one visually discernable positive affirmation as to whether the port is or is not pressure rated for the upcoming procedure.

In another particularly preferred mode, the identification marker is imparted on the cap member in its engagement on the catheter. The clip or cap member in this mode is formed larger for two reasons. First a larger surface area provides an area to print or form the triangle or other x-ray discernible symbol is a reasonably large fashion.

A second reason for the larger cap member is the provision of one or a plurality of finger engageable recesses or ridges formed on the surface of planar members extending from and communicating with the typically cylindrical cap body.

The planar members extending from the catheter engaged clip add utility in a number of ways. First, the planar protrusions provide a large surface to allow the user to better grip the cap between finger and thumb, when engaging the cap to catheter as described previously. Further as noted, the larger surface of the planar members provide a distinguishable location at or near the implanted port to impart the identification marker ink.

As an additional safety protocol, the software which controls the CT scan or other X-ray procedure may be programmed with image recognition program to be employed prior to the procedure moving forward. In this mode, the scanner or x-ray machine would be adapted to initially seek out the port and identify the marker in an initial scan of the patient before allowing the medical professional to continue with the procedure. Once identified by software adapted to recognize acceptable identifiers engaged to the port, a microprocessor will allow the employment of the next procedural step which would involve a powered injection to be communicated through the cover and into the reservoir of the port under high pressure.

Still further, the markers so engaged to or near the port, may be cross referenced with a database of pressure ratings. This would allow for the employment of multiple ports with higher and lower pressure ratings wherein a triangular shape for example would verify on pressure rating and a rectangular shape would verify a different pressure rating.

Even further, another identification marker may be employed in the form of a Radio-frequency identification (RFID) transponder. The technology can be used for automatically identifying the port as high pressure or otherwise. The relatively small RFID employing combined radio receiver and transmitter, or employing other audio or visual means for reporting, will thereby communicated identity information over a short distance, when energized by a detector placed close to the RFID antennas.

When configured to transmit a message, the RFID when energized by the RF field placed proximate to its antennas, will transmit numbers and/or text held in memory. The transmissions from an energized RFID can be read from several meters away and beyond the line of sight of the reader. The RFID tags can be programmed and hold information such as the port serial number, brand, install date, and pressure rating, during the manufacturing process. Thereafter, when implanted in a patient in combination with a pressure port, the RFID when energized by a reader device or other means of RF generation of sufficient power to energize the RFID, will transmit the stored information such as the noted serial number and high pressure rating along with other stored information.

Using an interface and software adapted to the task, this information could be automatically logged to a patient's chart, and/or can be employed in combination with software controlling the pressure pump, to enable the high pressure pump only when a high pressure rating is determined.

In an additional favored mode of the device herein, in addition to the RFID when energized, there may also be operatively engaged with the RFID, or independently activated or operated, one or both of an audio or visual reporting component, which will provide sonic and or visual affirmation when activated by either an RFID scanner or other means to activate an audio or visual report from outside the body of the patient. In this mode of operation, alone, or in combination with the RF transmission of data above, a electronic sound generator or beeper, or even a speaker capable of synthetic speech, can be also energized to make a sound discernible through the skin which would provide a sonic signal discernible by medical professionals without computers or x-rays, that the port is high pressure. Such a simple sound-based confirmation would be extremely useful in medical facilities without an x-ray but a need to use high pressure ports on patients. In addition to the electronic sound generator such as a buzzer or beeper, a small speaker engaged with an amplifier on the RFID or engaged with it, and a memory chip holding speech sounds in ROM, could combine to speak the words "high pressure" when the RFID is energized.

As noted, another mode of pressure port pressure from the exterior of the patient body is an LED operatively engaged to illuminate when the RFID circuit is energized. Such products are commercially available for instance from the Montie Design. LED's exist which are tremendously bright at low power and capable of illumination independently with their own remotely located operation component or concurrently when the RFID circuit is energized by RF energy sufficiently to be seen through the skin of the patient. From a small red dot visible through the skin to a series of LED's which render a red triangle through the skin, this visible means to determine a high pressure rating also needs no x-ray to provide the medical technician with confirmation of high pressure ratings. A light transmitting LED also would work well in instances where an X-ray is not convenient. It would also be preferred in some cases to employ a signaling scheme with the LED illumination. This can be in a similar fashion to Morse code where the LED will illuminate a specific number of times to confirm high pressure which will eliminate the possibility a manufacturer of a low pressure port might have an illuminating LED upon it could be mistaken. A set number of individual illuminations and darkenings signifying high pressure, such as three blinks, would be desirable. Further, both the sonic reporting and LED reporting, could also be used to simply save power and machine-use of the x-ray machine or CT scanner to simply ascertain the port rating. In this fashion, the CT scanner or x-Ray need not be employed since the LED, Sonic generator, or RFID, in combinations would provide a dual confirmation of the presence of a high pressure port. Further, with an RF transmission, or light through the skin, or sound transmitted through the skin, the user has three independent means to ascertain a high pressure rating of the implanted port.

The ability to view a marker engaged to or upon the implanted port or receive port information via transmitted data, sound, or light from LED's controlled in concert with energized RFID's, will thus provide a plurality of independent means to determine a proper pressure rating of the port. A sound can be generated, a light stream or plurality of blinks visible through the skin can be initiated, or an RF message can be transmitted and displayed on a computer screen. All three modes independently confirming that an implanted port, hidden under the patient's skin, is rated for the pressure to which it will be exposed in an upcoming procedure.

Yet another mode of visual confirmation of high pressure rating is available using another mode of the device herein wherein the RFID employs RF antennas which are shaped as triangles, or other easily discernable shapes which signify a high pressure port. The triangle of the antenna is metallic and will appear very distinct on an x-ray, thereby verifying using a symbol that the port is high pressure rated. The triangular antennas, the LED, the data transmission from the RFID, the sound transmitted, and the triangular member positioned on the clip, form a group of identifiers which all be employed singularly, or in combinations of all or any individual member of the group with any other, to provide one or a plurality of individual identifiers for a high pressure port. Further, it is anticipated that they may be used alone or in combination with the physical markers provided by a triangular metal member positioned in the reservoir of the port, or positioned on the clip engaged to the catheter o the port. This employment of icons and shapes such as a triangle will also allow technicians in countries where reading may be a challenge, and easy manner to visually confirm the presence of a high pressure port.

Further, in all preferred modes it is additionally preferred that the RFID may include a wideband transmission antenna element to allow the RFID and or a second transmitter to singularly or concurrently broadcast on multiple frequencies such as needed for bluetooth and WiFi. As the RFID is read or energized with a scanner, the transmitted information such as port serial number, brand, lot, manufacture date, install date, and pressure rating may be transmitted to a physicians electronic database and/or computer screen such that the information can be visually displayed. If the device employs an antenna capable of concurrent broadcasts in multiple frequencies a plurality of electronic input needs may be met such as broadcasting on bluetooth to input information to the patient chart, and wifi to transmit the information to a remote physician or medical database being served by a wireless router.

The foregoing has outlined rather broadly the more pertinent and important features of the device and method herein employing X-ray discernable markers upon or within implantable ports in order that the detailed description of the invention that follows may be better understood so that the present contribution to the art may be more fully appreciated.

Additional features of the invention may be described hereinafter which form the subject of the claims of the invention. It should be appreciated by those skilled in the art that the conception and the disclosed specific embodiments may be readily utilized as a basis for modifying or designing other X-ray discernable marking systems for implanted ports for carrying out the same purposes of the present invention. It should also be realized by those skilled in the art that such equivalent constructions and methods do not depart from the spirit and scope of the invention as set forth in the appended claims.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

THE OBJECTS OF THE INVENTION

It is, therefore, an object of the present invention to provide a computer displayed visual means to determine if an implanted and skin-covered port is power-rated for engagement to high pressure.

It is another object of this invention to provide such a device and method that may be easily incorporated into existing implantable ports and be identified with the installed base of medical equipment at medical facilities.

It is yet another object of this invention, to employ one or a plurality of such identifiable pressure rating markers which may be identified by a computer running software adapted to the task and thereby prevent accidental injection in a subsequent step if the proper pressure rating is not discerned.

It is still another object of the invention to provide a failsafe mechanism for determining the two means of pressure identification, wherein if the two means are not ascertained, the CT scan and/or power injection will be deactivated.

It is yet still another object of the invention to provide a conduit cap employing finger engageable gripping means and sized to hold symbols identifying the high pressure port.

Another object of the invention is to provide one or a combination of nonferrous metal, high density ceramic, teflon, or other x-ray excitable polymer identification marker which are easily discerned from the surrounding port body.

A further object of the invention is to provide a non ferrous metal, high density ceramic, x-ray excitable polymer identification marker in the form of one or a combination of alphanumeric characters or symbols/icons imparted on one or a combination of the body of the port, the cap, or the conduit.

Still another object of the invention is to provide a RFID identification marker imparted on one or a combination of the body of the port, the cap, or the conduit.

A still further object of the invention, is the provision of a concurrent means of multiple determination of the presence of a high pressure port using one or a plurality of a wireless, a visual signal and/or a sonic signal which identify the port as high pressure and which may be discerned through the user's skin.

Yet another object of the invention is the employment of discernible signals and figures which may be discerned by a reading-challenged staff which allow them to identify a high pressure port without the need to read.

The foregoing has outlined some of the more pertinent objects of the invention. These objects should be construed to be merely illustrative of some of the more prominent features and applications of the intended invention. Many other beneficial results can be attained by applying the disclosed method and device in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF DESCRIPTION OF THE DRAWINGS

The accompanying drawings, which are incorporated in and form a part of this specification, illustrate embodiments of the invention and together with the detailed description, serve to explain the principles of this invention.

FIG. 4 shows an perspective view of a preferred mode of the device wherein a finger engageable cap member having protruding planar members employs the identification marker.

FIG. 5 shows a top view of the device of FIG. 4 in another preferred mode wherein the identification marker is imparted on the septum, also providing a substantially larger finger engageable cap member FIG. 6 shows a bottom view of the device of FIG. 4 in still another preferred mode wherein the identification marker is imparted on the bottom surface.

FIG. 7 shows still yet another particularly preferred mode of the device employing a dual port system with the identification marker imparted on the body of the port.

FIG. 8 shows a mode of the device employing an RFID reader/energizer to elicit a data transmission from the RFID engaged with the device on the port body or catheter engaged clip.

FIG. 9 depicts an energizable RFID configured to report electronically and a means to illuminate through the skin such as an LED visible through the skin and or activate an sonic alarm such as a buzzer or beeper.

FIG. 10 shows and RFID, employable on the body of the device or clip, having antennas configured in segments to yield an x ray discernible triangular shape which would be visible on X-ray to identify the port.

FIG. 11 shows an overhead view of a port device employing a clip engaged upon the catheter having an RFID positioned for less interference of the body of the port during energizing as in FIG. 9 and a triangular marker thereon.

FIG. 12 depicts a port device having an RFID such as that of FIG. 9 having one or both antennas configured with segments yielding the depiction of triangles which are visible on X-ray to confirm pump pressure ratings which as with others can be on the clip or the body.

DETAILED DESCRIPTION OF THE PREFERRED EMBODIMENTS

Figure 1:
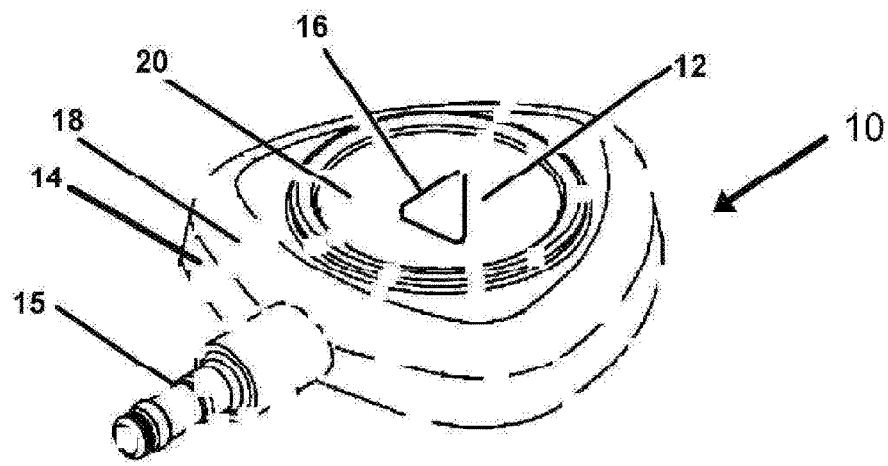
FIG. 1 depicts a perspective view of the device herein engaged to, or floating within an interior cavity or the reservoir of an implanted port shown in dotted line.

Referring now to the drawings 1-12, wherein similar parts of the invention are identified by like reference numerals, the device 10 as shown in FIG. 1 is seen having a symbol shaped marker 16 engaged to, or preferably floating within an interior cavity 12 of the body of a port 14 shown in dotted line. The marker 16 formed of metal such as stainless steel or one of the other noted discernible markers individually or in combination of the device 10 will be produced in combination with a high pressure port 14 and deployed in a conventional sterile container for implantation. Such other materials which are highly discernible from the surrounding tissue and polymeric material forming the port and/or the septum, are those that are excitable by x rays such as ceramics such as gadolinium oxysulfide, and in particular silicon nitride, Zirconium and zirconium Oxide and synthetics such as teflon.

An elongated conduit forming the outlet 15 of the port 14 is engageable to a catheter 23 or other device providing a lumen which is placed in sealed communication with a blood vessel of the patient. Any such implanted port 14 may employ any or all of the discernible markers enabling an identification of the device 10 herein as a high pressure port. The metal or other material discernible easily from the plastic body, such as a member marker 16 is engaged by the inclusion of the marker 16 in an engagement to the body 18 of the port 14, or more preferably by a positioning within an interior cavity 12 of the port 14 which will not require adhesive or heating or other engagement means that could damage the wall or other surfaces of the high pressure port. Such positioning without attachment provides a means to protect against an accidental damaging of the walls forming the port or its parts which must maintain high pressure capability.

Figure 2:
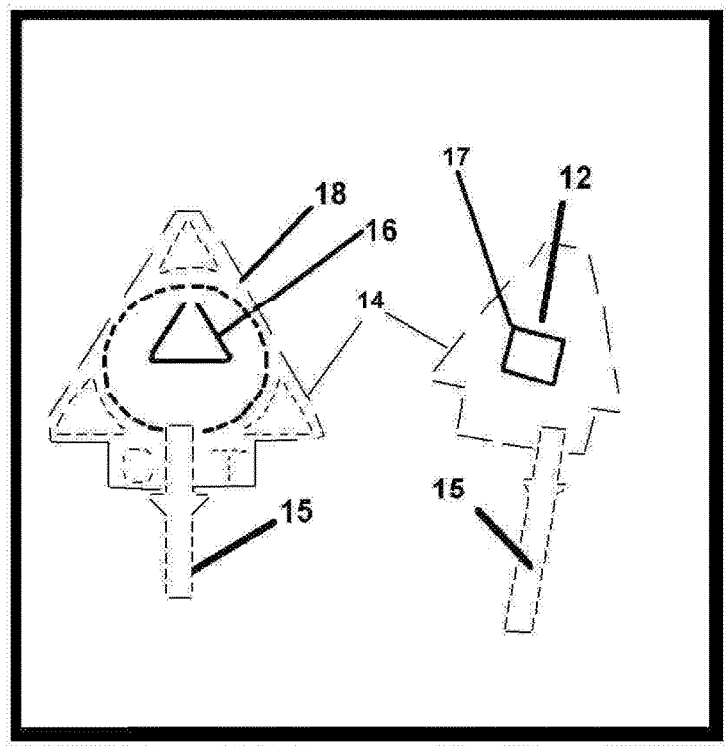
FIG. 2 depicts an X-ray of the device of FIG. 1 wherein the marker is rendered visible by a human or computer with operative recognition software, within the implanted port, and showing the device positioned within a reservoir under the septum.

As noted, the marker 16 is best formed of a metal or another material that is easily visually discernable from surrounding plastic material of the device, by the eye of a viewer of an X-ray as shown in FIG. 2. Such materials may include one or a combination of marker materials from a group including non ferrous metals such as nitinol, tungsten, titanium, stainless steel, and synthetic or ceramic materials such as teflon, silicon nitride, Zirconium, gadolinium oxysulfide or inks formed of a bio-compatible carrier containing one or a combination of the x-ray discernable materials noted herein which may be printed or adhered to the port 14, or other materials which will contrast with surrounding tissue and port materials to show on an X-ray.

In a preferred mode of the invention, the marker 16 may be a formed from a solid piece of metal material in a non-letter symbol. In other modes it may be painted or appliqued to the port 14 carefully so as to not damage it during manufacturing or long storage.

Additionally should the port 14 have multiple pressure ratings for differing procedures, indicia indicating the pressure rating for the port 14 may be included in the marker 16, or the marker 16 itself may be shaped differently such as the triangle marker 16 indicating a high pressure rating or a rectangular shaped marker 17 indicating a different pressure rating, each of which are cross referenced to a specific pressure rating. As noted above, it is preferred that the marker 16 be a symbol so the user need not have to read or discern any letters or numbers or language and risk misreading, or be unable to read them. Further, because a symbol is recognizable without a need for translation or reading ability, it is employable as a marker in any country, and any medical facility no matter the local language or ability of the technicians to read.

Positioned unattached within the body of the port 14, the marker 16 identifying the disclosed device 10 in combination with a port 14, will be clearly visible on an X-ray 17 as shown in FIG. 2. In one mode in FIG. 2 the marker 16 is engaged to the body 18 of the port 14 and in another image in the X-ray the marker 16 is shown floating within an interior cavity 12 below the septum 20 through which a needle penetrates to communicate an injection of a volume of fluid under high pressure to the port 14 in a medical procedure such as a CT scan. This floating mode allows for inclusion of the marker with the device, without the need to attach it and risk damage from heat, inks, or corrosion during long term storage as might occur if welded on, heated on, or glued onto the device.

Figure 3:
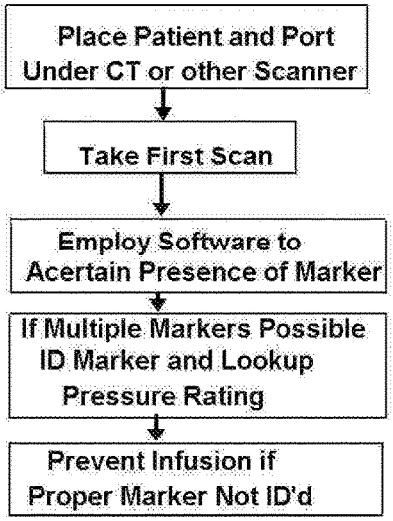
FIG. 3 depicts graphically a method of implementation of the device in a method to prevent high pressure injections to ports not recognized as capable of handling the intended pressure.

As depicted FIG. 3 a method of implementation employing the marker 16 is shown providing a means to prevent high pressure injections to ports not recognized as capable of handling the intended pressure may be employed with the device 10. As noted the software running the CT scanning device, or other X-ray device, or running on the medical facility computer system, may be adapted for use during medical procedures which require a positive identification of a high pressure rated port 14.

The software will employ the scanner to run an initial scan of the patient and use image recognition software to ascertain the presence of the marker 16, prior to allowing the technician to inject the port 14 under high pressure in a second step. Because the port 14 is easily visually identifiable for pressure rating based on the marker 16 or 17 discerned, multiple ports 14 with multiple pressure ratings might be use without worry. Since ports 14 which must survive higher pressures generally cost more, the employment of markers 16 or 17 in solid or printed format which provide visual confirmation of the rating of the hidden port 14, will allow for less expensive ports 14 to be employed where subsequent pressures are anticipated to be lower.

If the software mode of the method herein is employed, the CT Scanner or other software and wireless adapted device would in a first step take an initial scan and employ visual recognition software to discern shape of the marker 16 or 17. In a second step the software adapted to the task and running on a microprocessor, using the discerned shape, will calculate if the shape discerned is the shape employed to designate an acceptable high pressure-rated port. If the proper port is ascertained as present, the injection would be permitted. Software controlled locks can be employed to lock out the high pressure injection until confirmation is ascertained of the port.

If more than one shape of the identifier is employed on multiple ports, due to multiple ratings on multiple ports, the software and microprocessor would use the initial scan to ascertain the identifier present, and the would then match the ascertained shape of the identifier in the patient, to a relational database of identifier shapes. Using the match, the shape as related to a predetermined pressure rating for ports bearing the recognized identifier will be determined. Once the identification of the port imaged is determined, the procedure would only be allowed to proceed to the high pressure injection, if the proper pressure rating is discerned from the discerned identifier ascertained from the data regarding its rating which is accessed by the software in the identification step with a relational database.

FIG. 4 shows an additional preferred mode of markers in combination with a single port 14 yielding a device 10. In the figure there is depicted the port 14 and fluid communication means such as a catheter 34 or similar lumen engaged. The catheter 34 is shown employing a particularly preferred cap 21 of this invention which is secured to the catheter 34 to aid its engagement to the outlet 15. As mentioned previously a conventional cap (not shown) is typically a small and hard to handle cylindrical body coaxially and slidably engaged over the catheter 34 and is used to further secure the distal end 35 of the catheter 34 to the outlet 15 of the port 14.

The preferred cap 21 of the present invention however, employs one or a plurality of projecting members 22 engaged to and communicating with a cylindrical body 25. The projecting member 22 provide a large surface area as a means to grip and maneuver the cap 21 such as with the thumb and forefinger (not shown). Further the surface of the planar member 22 may be employed as a mount for an identification marker 23, such as lettering shown, or using symbols such as a triangle as noted above to allow wider use in different countries. Materials for the marker would be those yielding a high contrast from surrounding tissue and plastic.

The marker 23, in this mode, may be inlayed solid metal or ink infused with one or a combination of marker materials from a group including a nonferrous metal such as nitinol, tungsten, titanium, stainless steel, and synthetic or ceramic materials such as teflon, silicon nitride, Zirconium, gadolinium oxysulfide or inks formed of a bio-compatible carrier containing one or a combination of the x-ray discernable materials noted herein high density ceramic, or an x-ray excitable polymer or plastic such as teflon, which will yield a contrast on an x-ray with the surround material.

Such a marker 23 will be easily distinguishable in an MRI or x-ray by being adjacent to the thicker body thereby providing a means to identify the port 14 as high pressure or otherwise. The maker 23 of such material may include alphanumeric characters, or preferably non alphanumeric symbolic marker 16, 17 such as a triangle shown previously. By positioning the marker on the cap, which provides a means to anchor the high pressure catheter to the body, the risk of damaging the plastic walls of the body is eliminated as is the risk of damage from long term storage with inks applied to the body of the device. As noted, the marker 23 may be applied using one or a plurality of the aforementioned x-ray discernible materials yielding high contrast from surrounding materials.

FIG. 5 shows a top view of a device 10 of FIG. 4 however in another preferred mode wherein the infused ink alphanumeric or a symbolic or iconic marker 23 is imparted on the septum 20 of the port 14 alone or in combination with such on the body of the catheter 34. The marker would be as with all markers herein, formed of one or a combination of the aforementioned marker materials. It must be noted that the mode currently shown as well as the other modes disclosed may be employed separately or in combination with one another and should therefor not be considered limiting by the figures.

Further shown in the FIG. 5 is yet another preferred mode of the cap member 21 wherein the cap 21 is a substantially planar body 26 employing a finger ingressable recess 28 providing means to better grip the cap 21 for operative employment as described previously. The cap 21 is shown in the engaged as used mode, engaged to the catheter 34 and wherein the distal end 35 of the catheter 34 is engaged to the outlet 15 of the port 14 while the cap 21 is additionally frictionally and slidably engaged over and providing a compression toward the catheter-engaged outlet 15.

A still further means for identification of the port 14 is provided via the employment of an electronically activated tag having an RFID 24 shown engaged to the cap 21. The RFID 24 employed concurrently with an RFID reader 41 which will allow a medical professional to merely scan over the users chest or other probable location of the port 14 and receive port 14 information transmitted via radio frequency (RF). Such information may include, but is not limited to, the port serial number, install date, and the pressure rating. As shown in FIG. 8, such radio frequency information may also be received by Wi-Fi, bluetooth, or other transmitted means to communicate directly with a computer or the CT scanner or power injector as a fail safe means. For example, if RFID returns that the port 14 is not high pressure rated, the CT or injector will remain locked and deactivated. This is commonly referred to as a 'Go, No-go' type failsafe system.

It is within the scope of the present invention that the infused ink alphanumeric marker 23 may be formed of one or a combination of marker materials from a group of marker materials including non ferrous metals, such as nitinol, tungsten, titanium, stainless steel, and synthetic or ceramic materials such as teflon, silicon nitride, Zirconium, gadolinium oxysulfide or inks formed of a bio-compatible carrier containing one or a combination of the x-ray discernable materials noted herein, and be imparted on the body 18 of the port 14 such as shown in FIG. 6. In the figures, the marker 23 provides a first means to discern a pressure rating and the RFID 24 provides another means to discern a pressure rating. The marker 23 is carefully imparted on the bottom surface 19 of the body 18.

Again, it must be noted that, the marker 23 may preferably instead be an iconic or symbolic marker 16, 17 such as a triangle as previously shown and formed as noted above from the marker materials group. A symbolic marker is more readably and positively discernible by nonreaders and even by readers since they may be sight impaired or without their reading glasses.

Shown in FIG. 7 is yet another preferred mode of the device 10 employing a dual system port 30 having a bifurcated outlet 32. The maker in the form of an RFID 24 such as those of FIGS. 9 and 10 provides means to discern pressure rating and is shown imparted on the top surface or engaged in a slot in the cap 21. There is an additional employed marker shown on top of the septum 20 as lettering. However, a symbol not requiring reading by a user can also be employed. As noted two discernible markers provide dual confirmation in all modes of the device without an x ray or CT scan needed.

FIG. 8 shows a mode of the body 14 of the device employing an RFID 24 in a conventional capacity which when energized by the reader 41 transmits a data from the RFID 24 and RAM or ROM or other means for electronic storage engaged with the within the RFID and located on the port body or catheter engaged clip. The transmit and receive antennas for the RFID 24 are shaped in the triangle symbol and are formed of metal adapted to receive RF energy from the reader 41 so they appear on an x-ray as a visual symbol confirming pressure rating. This combination provides dual confirmation of the pressure rating of the port without the need for exposing the patient to an x-ray or CT scan.

FIG. 9 depicts an energizable RFID 24 and other components configured to provide a naked-eye-visible, or clearly audible signal identifying its presence under a patient's skin. When energized by a reader 41 or other RF emitted transmission, the LED may either employ energy generated from the passive RFID board using energy generated from the RF, or the LED 43 or may have its own power supply and thereby be electronically activated to switch on and illuminate which will be visible through the skin of the patient if mounted in position adjacent thereto, thereby providing a visibly discernible signal, through the skin of the patient, of the hidden underlying port's high pressure readiness, without an x-ray or scan.

In combination or as an alternative, energizing the RFID 24 may concurrently cause activation of an electronic sound generator to activate a sonic alarm 45 such as a buzzer or beeper as well as an LED 43 as well as the RFID 24. The multiple signaling component configuration of the device 10 may be employed on any of the ports herein. This provides, in one pass, a triple certification of high pressure readiness.

FIG. 10 shows an RFID 24 having antennas 29 configured in segments to yield a triangular shape on an X-ray thereby providing the non alphanumeric symbol, which would be visible on X-ray to identify the port. The RFID 24 is shown with the LED 43 and alarm 45. It is particularly preferred in all modes of the device herein, that the RFID 24 be MRI-safe in that ferrous metal is minimized or eliminated from the structure. Consequently, it is particularly preferred that the antennas 29 and larger portions of the RFID 24 is formed of substantially non ferrous metal which will not be moved or dismounted by the forces of an MRI such as aluminum, copper, titanium or an alloy, tin, or nickel. These metals will not be attracted to the magnetic force, and will not heat substantially and will generally alone or in combinations and alloys receive and transmit a sufficient signal to and from the RFID.

As noted earlier, the RFID 24 may be placed on the catheter securement clip, to allow attachment to the port without attaching to the walls forming it which can cause damage during manufacture or long term storage which might not be noticed and potentially cause harm to a patient if such a wall failed during use.

As additionally noted, the RFID 24 may include a wideband broadcast antenna 29 for broadcasting upon multiple frequencies with one or a plurality of RF data streams, employing frequencies such as those associated with bluetooth and Wi-Fi transmissions. When energized by RF, the RFID would transmit information stored in ROM on the RFID 24 concerning the nature of the port. This dual broadcast may also be employed as a fail safe or as a means for transmission of a plurality of data streams about the device which will allow the RFID 24 to communicate for instance with a physician's medical record database configured to receive transmitted identification data, or a visual display means such as a computer or smartphone having software adapted to receive the information broadcast from the ROM or RAM of the RFID and convert it to a displayed image on the screen thereof.

FIG. 11 shows an overhead view of a port device employing the clip 21 engaged upon the catheter 34 and having an RFID 24 on or in a cavity in the clip 21 where such positioning will avoid potential damage of placing a marker on the body of the port and will also position it better to transmit and receive RF energy. The RFID 24 is as in FIG. 9 and a triangular marker is shown on another planar side of the clip.

FIG. 12 depicts a port device having an RFID 24 such as that of FIG. 10 having one or both antennas 29 configured with segments yielding the depiction of triangles which are visible on X-ray to confirm pump pressure ratings. The RFID 24 is also shown with the LED 43 and alarm 45. As noted, any of the audio, visual, or other discernable markers shown or describe herein, may be employed singularly or in combination with any other one or plurality of such markers.

While all of the fundamental characteristics and features of the disclosed device and method herein have been described herein, with reference to particular embodiments thereof, a latitude of modification, various changes and substitutions are intended in the foregoing disclosure and it will be apparent that in some instance, some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined herein.

What is claimed is:

1. An injection port for implantation under the skin of a patient, comprising:
    a body having an injectable reservoir for receiving fluid from an injection through a septum covering said reservoir;
    a cap said cap having a body portion positionable upon an exterior of a catheter and configured for securing said catheter to a fluid outlet from said body;
    a first marker, said first marker positioned upon a surface of a member extending from said body portion of said cap, said first marker formed of a marker material which is clearly discernable for a shape of said first marker from surrounding material in an X-ray image of said port when implanted in a patient; and
    said first marker when viewed upon said x-ray image of said injection port, correlating to a pressure rating of said injection port, wherein said pressure rating can be determined without removing said pressure port from said implantation.

2. The injection port of claim 1 additionally comprising:
    said first marker formed of a MRI-safe material including one or a combination of marker materials from a group including, MRI-safe materials including nitinol, tungsten, titanium, stainless steel, teflon, silicone nitride, Zirconium, gadolinium oxysulfide, and inks formed of a bio-compatible carrier and one or a combination of said marker materials; and
    the employment of such MRI-safe marker materials singularly or in combination thereby minimizing interaction of said injection port while implanted, with radiated energy during an MRI.

3. The injection port of claim 2 additionally comprising:
    said first marker having a non alphanumeric shape clearly identifiable in said x-ray image; and
    said shape discernible to indicate a pressure rating for said injection port to viewers speaking and reading any language.

4. The injection port of claim 3 additionally comprising:
    a second marker being an RFID having electronic memory and a data processor configured to broadcast port identification information when energized from outside a patients body by RF; and
    a receiving device configured to patient's said broadcast port information and provide a video display discernible by a user to ascertain said port identification information.

5. The injection port of claim 4 additionally comprising:
    one or a plurality of supplemental markers from a group of supplemental markers including, an led in electrical communication with said RFID which illuminates to communicate light through the patient's skin when said RFID is energized by said RF, a electronic sound generator in electrical communication with said RFID which communicates a sound through the patient's skin when said RFID is energized by said RF, a shape of an antenna engaged to said RFID, said antenna shape discernible in an x-ray to identify a pressure rating for said pressure port, and said RFID configured to broadcast identification information to a receiving display device when energized by said RF.

6. The injection port of claim 2 additionally comprising:
    a second marker being an RFID having electronic memory and a data processor configured to broadcast port identification information when energized from outside a patient's body by RF; and
    a receiving device configured to receive said broadcast port information and provide a video display discernible by a user to ascertain said port identification information.

7. The injection port of claim 6 additionally comprising:
    one or a plurality of supplemental markers from a group of supplemental markers including, an LED in electrical communication with said RFID which illuminates to communicate light through the patient's skin when said RFID is energized by said RF, an electronic sound generator in electrical communication with said RFID which communicates a sound through the patient's skin when said RFID is energized by said RF, a shape of an antenna engaged to said RFID, said antenna shape discernible in an x-ray to identify a pressure rating for said pressure port, and said RFID configured to broadcast identification information to a receiving display device when energized by said RF.

8. The injection port of claim 1 additionally comprising:
    a second marker being an RFID having electronic memory and a data processor configured to broadcast port identification information when energized from outside a patient's body by RF; and
    a receiving device configured to receive said broadcast port information and provide a video display discernible by a user to ascertain said port identification information.

9. The injection port of claim 8 additionally comprising:
    one or a plurality of supplemental markers from a group of supplemental markers including, an LED in electrical communication with said RFID which illuminates to communicate light through the patient's skin when said RFID is energized by said RF, an electronic sound generator in electrical communication with said RFID which communicates a sound through the patient's skin when said RFID is energized by said RF, a shape of an antenna engaged to said RFID, said antenna shape discernible in an x-ray to identify a pressure rating for said pressure port, and said RFID configured to broadcast identification information to a receiving display device when energized by said RF.

10. The injection port of claim 8 additionally comprising:
a third marker, said third marker being an LED in electrical communication with said RFID which illuminates to communicate light emitted therefrom, through the patient's skin when said RFID is energized by RF energy; and said light emitting a light signal correlating to said pressure rating of said pressure port.

11. The injection port of claim 1 additionally comprising:
a second marker, said second marker being an LED in electrical communication with said RFID which illuminates to communicate light emitted therefrom through the patient's skin when said RFID is energized by RF energy; and said light emitting in a light sequence correlating to said pressure rating of said pressure port.

12. The injection port of claim 11 additionally comprising:
a third marker, said third marker being an electronic sound generator; and said electronic sound generator emitting a sound though the patient's skin correlating to said pressure rating of said pressure port.

* * * * *